US011944275B2

United States Patent
Shorer et al.

(10) Patent No.: US 11,944,275 B2
(45) Date of Patent: Apr. 2, 2024

(54) SYSTEM AND DEVICE FOR VIEWING OF A BODY PORTION

(71) Applicant: ScopeBug, Inc., Locust Valley, NY (US)

(72) Inventors: Oded Shorer, New York, NY (US); Or Ramot, Oranit (IL); Michael Noonan, Port Washington, NY (US); Jessica Walsh, Locust Valley, NY (US)

(73) Assignee: ScopeBug, Inc., Locust Valley, NY (US)

( * ) Notice: Subject to any disclaimer, the term of this patent is extended or adjusted under 35 U.S.C. 154(b) by 0 days.

(21) Appl. No.: 17/750,351

(22) Filed: May 22, 2022

(65) Prior Publication Data

US 2022/0369912 A1 Nov. 24, 2022

Related U.S. Application Data

(60) Provisional application No. 63/191,994, filed on May 22, 2021.

(51) Int. Cl.
| | |
|---|---|
| *A61B 1/00* | (2006.01) |
| *A61B 1/05* | (2006.01) |
| *A61B 1/06* | (2006.01) |
| *A61B 1/227* | (2006.01) |
| *A61B 1/233* | (2006.01) |
| *A61B 1/24* | (2006.01) |

(52) U.S. Cl.
CPC .......... *A61B 1/233* (2013.01); *A61B 1/00016* (2013.01); *A61B 1/00018* (2013.01); *A61B 1/00105* (2013.01); *A61B 1/00131* (2013.01); *A61B 1/05* (2013.01); *A61B 1/0607* (2013.01); *A61B 1/227* (2013.01); *A61B 1/24* (2013.01)

(58) Field of Classification Search
CPC ... A61B 1/05; A61B 1/00018; A61B 1/00131; A61B 1/233; A61B 1/227; A61B 1/00105; A61B 1/00108; A61B 1/24; A61B 1/00016; A61B 1/0607
See application file for complete search history.

(56) References Cited

U.S. PATENT DOCUMENTS

| | | | | |
|---|---|---|---|---|
| 2003/0228553 | A1* | 12/2003 | Mandelkern | A61B 1/0676 433/29 |
| 2005/0027168 | A1* | 2/2005 | Strom | A61B 1/227 600/200 |
| 2010/0171827 | A1* | 7/2010 | Wu | A61B 3/185 348/135 |

(Continued)

*Primary Examiner* — Timothy J Neal
(74) *Attorney, Agent, or Firm* — The Law Office of Joseph L. Felber

(57) ABSTRACT

A system for self-imaging a body portion includes a self-imaging device and an ancillary device that is attachable to the self-imaging device. The self-imaging device has a base member, a camera located within the base member and a guide element for transmitting light along a path extending between the camera and an exposed tip of the guide element that opens out of the self-imaging device at a given side of the device. The ancillary device is arranged to attach to the self-imaging device at said same given side while substantially not obstructing incoming light arriving towards the self-imaging device from being transmitted via the guide element towards the camera.

16 Claims, 5 Drawing Sheets

(56) References Cited

U.S. PATENT DOCUMENTS

Figure 1:
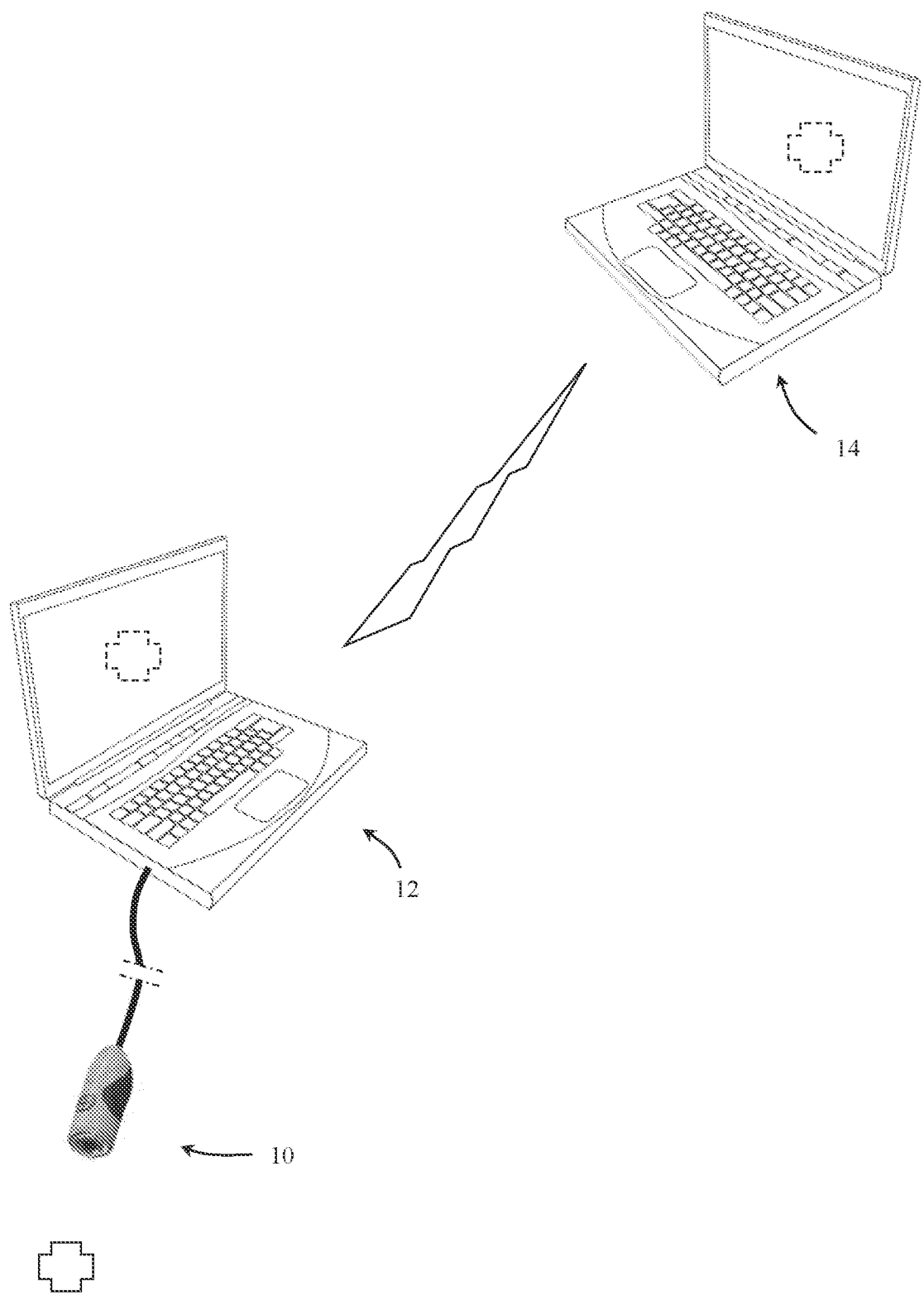

| | | | |
|---|---|---|---|
| 2011/0134234 A1* | 6/2011 | Kim | G02B 21/0008 |
| | | | 348/80 |
| 2014/0171743 A1* | 6/2014 | Heine | A61B 1/227 |
| | | | 600/200 |
| 2015/0118637 A1* | 4/2015 | Ou-Yang | A61B 1/00186 |
| | | | 433/29 |
| 2020/0054203 A1* | 2/2020 | Shreim | A61B 5/0075 |
| 2021/0127966 A1* | 5/2021 | Christiansen | A61B 1/24 |
| 2022/0133447 A1* | 5/2022 | Hansen | A61B 1/24 |
| | | | 382/128 |

* cited by examiner

SYSTEM AND DEVICE FOR VIEWING OF A BODY PORTION

FIELD OF THE INVENTION

Embodiments of the present disclosure generally relate to devices and systems for viewing a body portion, such as an orifice or surface of the body, and more particularly to devices and systems for providing self-imaged views of a body portion.

BACKGROUND OF THE INVENTION

The direct inspection of a body portion such as internal structures of the body has been used for thousands of years in the diagnosis of medical disorders. This has been further enhanced by improvements in lighting and fiberoptic technology, and more recently, the ability to capture still and moving images in digital form for viewing at a later time or transfer to a medical professional at a remote location. Additionally, the use of telemedicine in the care of patients has grown rapidly in the past decade. This trend will likely continue with advancements of digital communications technologies.

SUMMARY OF THE INVENTION

In one aspect, the present disclosure provides a device for self-imaging at least a body cavity such as a nasal cavity, nasopharynx and lateral nasal wall regions. The nasal self-imaging device may include guide elements spaced apart from one another and configured to be at least partially inserted into respective nostrils of a patient, and a flexible connector element attached to and extending between the guide elements. Each guide element includes an aperture extending therethrough from a base end to a tip end of the guide element. At least one camera is disposed within one or more apertures to allow recording images or videos of the nasal cavities of a patient. Additionally, the self-imaging device can include a light source. The light source may include one or more filters for different light wavelengths such as infrared, and ultraviolet light, or the light source may emit light in the visible spectrum. In one embodiment, there are also filters allowing for chemiluminescence or tissue autofluorescence capabilities. Chemiluminescence or tissue autofluorescence capabilities may also be achieved using additional one or more lighting sources disposed in proximity to one or more lenses. The camera has at least one lens wherein the angle of the lens can be controlled by a processing device or a separate hand-held controller. In one embodiment, the camera may have two or more lenses functioning in tandem for better visualization of the nasal cavity. In one embodiment, the one or more camera lenses has the capability to zoom in and out, telescope or rotate, making the subjects in the field appear between 1 cm and 10 cm closer.

In another aspect, the present disclosure provides a system for self-imaging of one or more nasal cavities of a patient's nose. The system includes a nasal self-imaging device including a pair of guide elements spaced apart from one another, and a flexible connector element attached to and extending between the guide elements. Each guide element includes an aperture extending therethrough from a base end to a tip end of the guide element. At least one camera is disposed in one or more apertures. The system also includes a processor device interacting with the self-imaging device. The processor device can be operated by a patient to direct the nasal self-imaging device to record images or videos. Self-recorded images or videos can be stored, displayed, edited and transmitted using the processing device. In an embodiment, the processor device can interact with the self-imaging device wirelessly through a Bluetooth connection.

In yet another aspect, the present disclosure provides a device for self-imaging a patient's ear canal and tympanic membrane. The ear self-imaging device includes an earpod configured to be at least partially inserted into an ear of a patient. There can be a left and a right earpods adapted for the left and the right ears, respectively. Said earpod may include one or more apertures extending therethrough from an exterior surface to an interior space of the earpod. At least one camera is disposed at least partially within the one or more apertures to allow for recording of images or videos of the ear canal of a patient. The ear self-imaging device can include a light source disposed in proximity to the camera. The light source may include one or more filters for different light wavelengths such as infrared, and ultraviolet light, or the light source may emit light in the visible spectrum. In one embodiment, there are also filters allowing for chemiluminescence or tissue autofluorescence capabilities. Chemiluminescence or tissue autofluorescence capabilities may also be achieved using additional one or more lighting sources disposed in proximity to one or more camera lenses. The camera has at least one lens wherein the angle of the lens can be controlled by a processing device or a separate hand-held controller. In one embodiment, the camera may have two or more lenses functioning in tandem for better visualization of the ear canal. In one embodiment, the one or more camera lenses has the capability to zoom in and out, telescope or rotate, making the subjects in the field appear between 1 cm and 10 cm closer.

In another aspect, the present disclosure provides a system for self-imaging of a patient's ear canal and tympanic membrane. The system includes an ear self-imaging device including an earpod configured to be at least partially inserted into an ear of a patient. There can be a left and a right earpod adapted for the left and the right ears, respectively. Said earpod includes one or more apertures extending therethrough from an exterior surface to an interior space of the earpod. At least one camera is disposed at least partially within one or more apertures to allow for recording of images or videos of the ear canal of a patient. The ear self-imaging device can include a light source disposed in proximity to the camera. The system also includes a processor device interacting with the self-imaging device. The processor device can be operated by a patient to direct the ear self-imaging device to record images or videos. Self-recorded images or videos can be stored, displayed, edited and transmitted using the processing device. In an ideal embodiment, the processor device can interact with the self-imaging device wirelessly through a Bluetooth connection. The processing device can be a smart phone or a computer. The system may further include a software package adapted to function on a processor device to facilitate visualization of a patient's ear canal.

In yet another aspect, the present disclosure provides a device for self-imaging a patient's oral cavity and oropharynx regions. The oral self-imaging device includes a mouth guard configured to be at least partially inserted into the mouth of a patient. Said mouth guard includes one or more apertures extending therethrough from an exterior surface to an interior surface of the mouth guard. At least one camera is disposed at least partially within one or more apertures to allow for record ing of images or videos of the oral cavity of a patient.

The oral self-imaging device further includes a tongue depressor element attached to an interior surface of the mouth guard and extending into a patient's mouth. Additionally, the self-imaging device can include a light source. The light source may include one or more filters for different light wavelengths such as infrared, and ultraviolet light, or the light source may emit light in the visible spectrum. In one embodiment, there are also filters allowing for chemiluminescence or tissue autofluorescence capabilities. Chemiluminescence or tissue autofluorescence capabilities may also be achieved using additional one or more lighting sources disposed in proximity to one or more lenses.

The camera has at least one lens wherein the angle of the lens can be controlled by a processing device or a separate hand-held controller. In one embodiment, the camera may have two or more lenses functioning in tandem for better visualization of the oral cavity. In one embodiment, the one or more camera lenses has the capability to zoom in and out, telescope or rotate, making the subjects in the field appear between 1 cm and 10 cm closer.

In another aspect, the present disclosure provides a system for self-imaging of a person's oral cavity. The system includes an oral self-imaging device including a mouth guard configured to be at least partially inserted into the mouth of a patient. Said mouth guard includes one or more aperture extending therethrough from an exterior surface to an interior surface of the mouth guard. At least one camera is disposed at least partially within one or more apertures to allow for recording of images or videos of the oral cavity of a patient. The oral self-imaging device further includes a tongue depressor element attached to an interior surface of the mouth guard and extending into a patient's mouth. The system also includes a processor device interacting with the self-imaging device. The processor device can be operated by a patient to direct the oral self-imaging device to record images or videos. Self-recorded images or videos can be stored, displayed, edited and transmitted using the processing device. In an ideal embodiment, the processor device can interact with the self-imaging device wirelessly through a Bluetooth connection. The system may further include a software package adapted to function on a processor device to facilitate visualization of a patient's oral cavity.

BRIEF DESCRIPTION IF THE FIGURES

The detailed description is set forth with reference to the accompanying drawings, which are not necessarily drawn to scale. Use of the same reference numerals indicates similar or identical items. Certain embodiments of the present disclosure may utilize elements, components, and/or configurations other than those illustrated in the drawings, and some elements, components, and/or configurations may not be present in certain embodiments.

Figure 2:
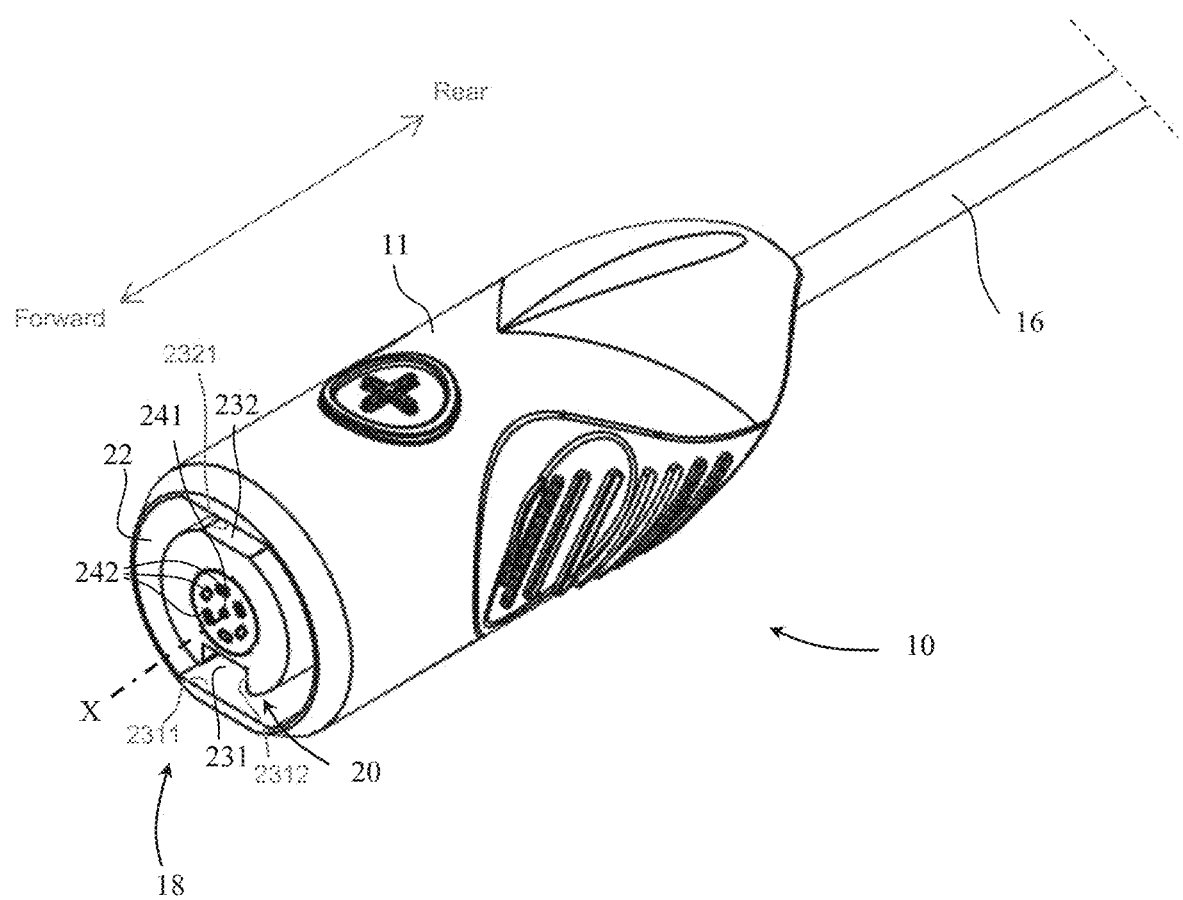
Figure 3A:
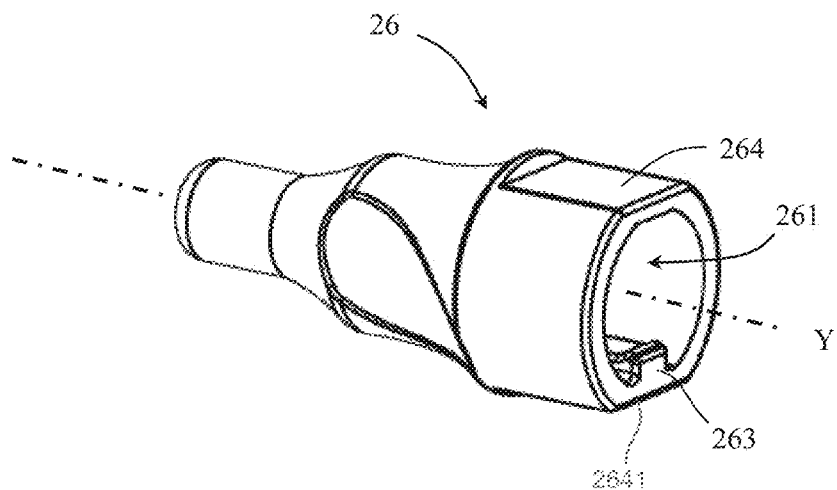
Figure 3B:
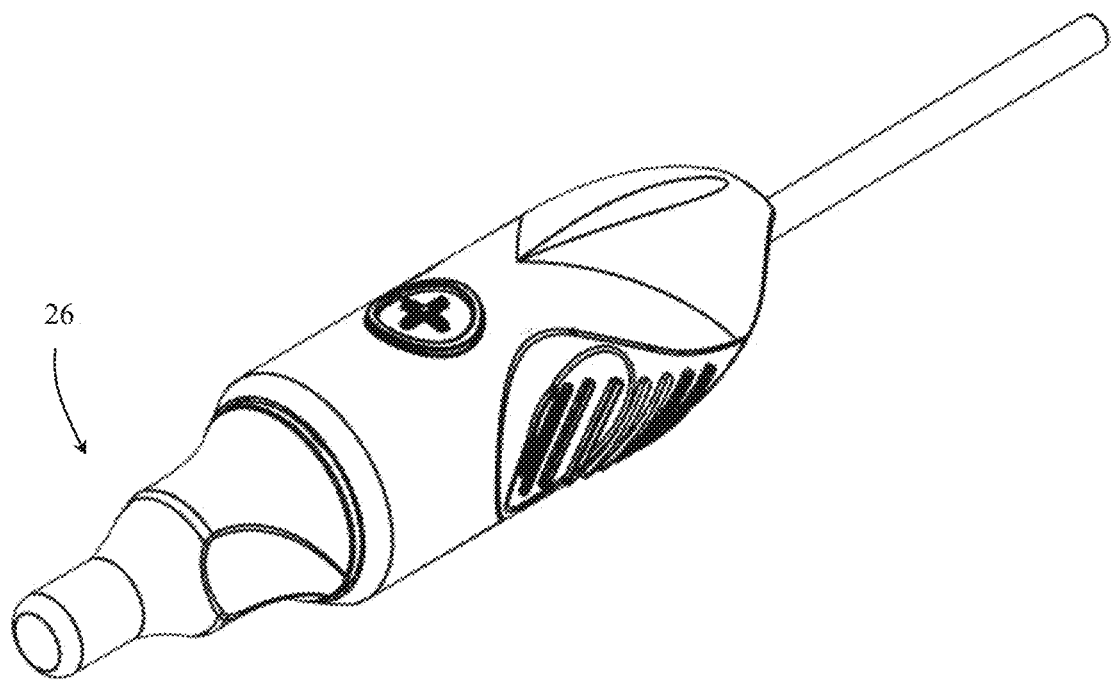
Figure 4A:
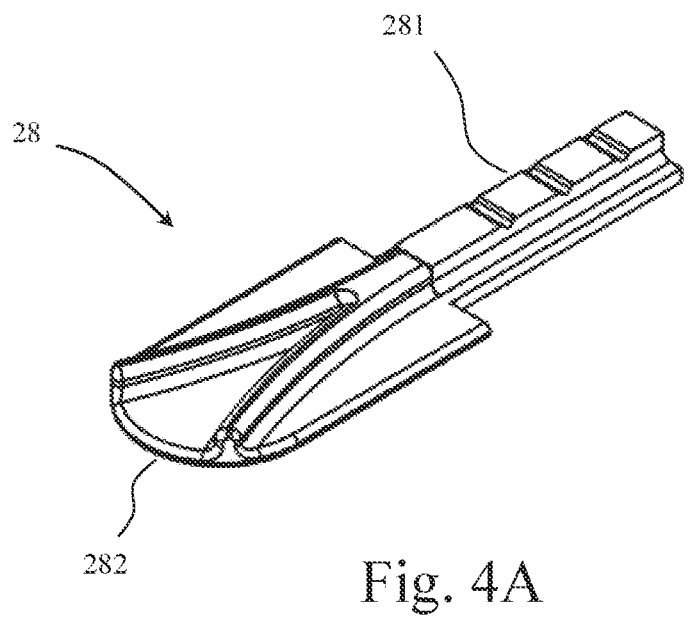
Figure 4B:
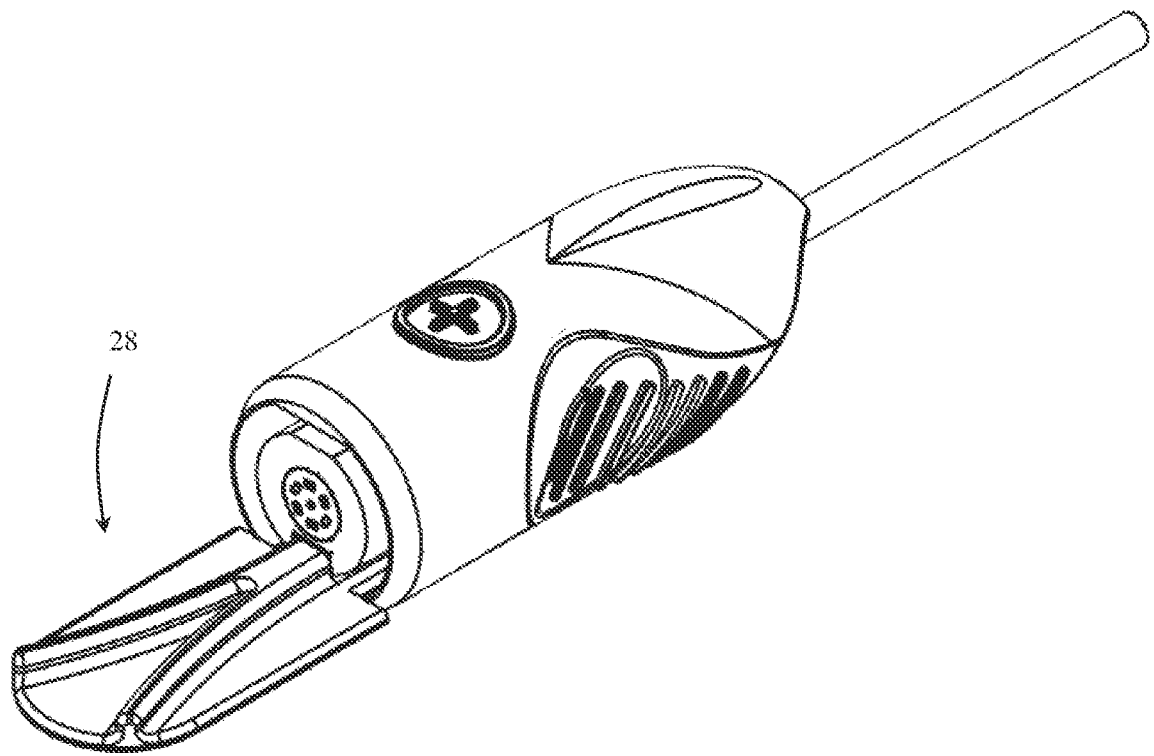
Figure 5A:
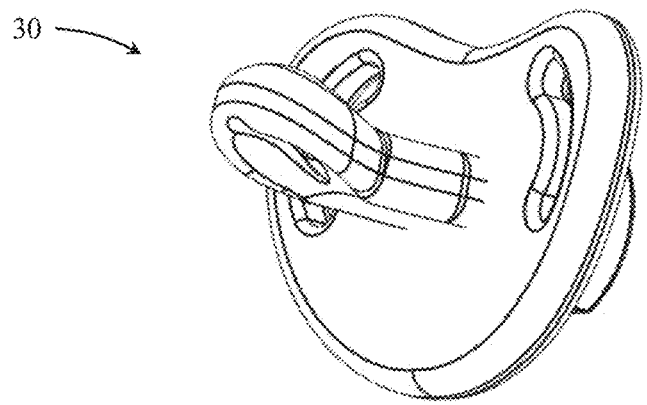
Figure 5B:
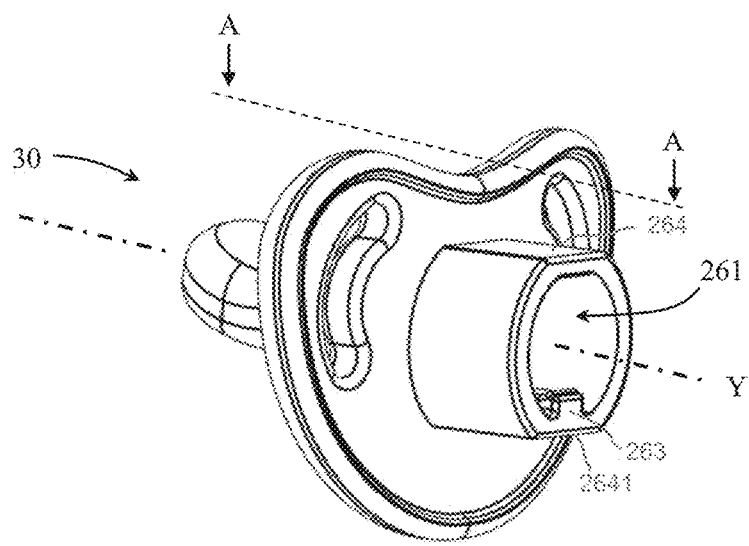
Figure 5C:
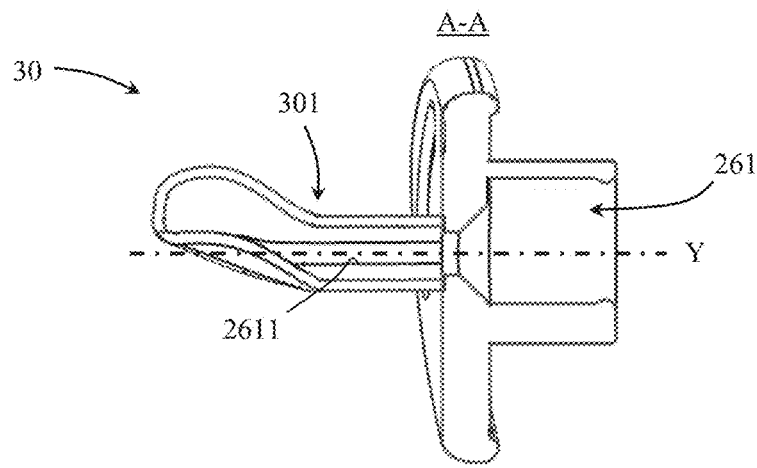

FIG. 1 schematically shows an embodiment of a self-imaging device connected to a local computing device, which is in communication with a remote computing device;

FIG. 2 schematically shows a closer view of an embodiment of a self-imaging device such as that seen in FIG. 1;

FIGS. 3A, 3B and 4A, 4B schematically show embodiments of a self-imaging device such as those seen in the former figures, coupled with ancillary members suitable for inspecting body portions; and FIGS. 5A to 5C schematically show an embodiment of another possible ancillary member suitable for inspecting body portions.

DETAILED DESCRIPTION OF THE INVENTION

Current devices used for capturing body portion or part images, such as endoscopes that are suited to capture internal body organs, are designed to be typically used by specially-trained medical professionals, and not by the average person. These current devices can be used for capturing internal images of lesions or abnormalities of e.g. the lining of the ear canal and tympanic membrane, lining of the mouth and throat, internal images from areas such as the nose (or the like). Regular untrained people who are concerned that they have a medical condition in a body part may resist going to have a medical checkup at a physician, perhaps due to fear of the physical exam, since they do not have easy access to reach a physician (etc.). The subject matter disclosed in the exemplary embodiment herein allows for the patient to capture and remotely transfer high-resolution images of the region of concern to a medical professional.

Devices, which patients can use at home, such as smartphones or GoPro devices, can be used for capturing images of the outer side of a body portion, such as the skin, but cannot conveniently provide adequate visualization of internal structures because of their size and shape. They are also unable to be manipulated in real time by a medical professional located remotely. Portable otoscopes for example for visualizing the ear canal and flashlights can be used to illuminate the internal structures of the ear, nose and mouth/throat region, but cannot capture these images and transfer to medical professionals. Capsule endoscopy, to visualize the gastrointestinal tract, which can be steered magnetically by a physician, is currently on the market, but is not practical for use in the regions described above. Ear buds and nasal cones are devices that fit comfortably in the ears and nose for audio listening and snoring, respectively, but neither have the ability to capture digital images.

In the following description, reference is made to the accompanying drawings that form a part hereof, and in which is shown by way of illustration specific example embodiments, which may be practiced. These example embodiments are described in detail to enable those skilled in the art to practice the devices and systems of the present disclosure, and it is to be understood that other embodiments may be utilized and that logical changes may be made without departing from the scope of the present disclosure. The following description of example embodiments is, therefore, not to be taken in a limited sense, as the scope of the present invention is defined by the appended claims.

Attention is drawn to FIG. 1 schematically illustrating an embodiment of a self-imaging device 10 that is connected to a local computing device 12. The local computing device 12 may in turn be in communication with a remote computing device 14 where professional personnel may be situated. Self-imaging device 10 can be used by regular untrained people possibly within their home environment for capturing visual data, such as images or video, of their body parts. Such visual data may be of lesions or abnormalities of e.g. the lining of the ear canal and tympanic membrane, lining of the mouth and throat, internal images from areas such as the nose (or the like). Such visual data may be communicated to a physician at the remote location for inspection, checkup or the like.

Attention is drawn to FIG. 2 schematically showing a closer view of an embodiment of a self-imaging device 10 such as that seen in FIG. 1. Self-imaging device 10 includes a base 11 that extends along an axis X that in this example is seen being coupled at its axial rear side to computing device 12 via a cable 16. Also seen is that the self-imaging device includes a coupling region 18 at an axial forward side of base 11.

The self-imaging device includes at its coupling region a hub 20 surrounded in this example by a peripheral slit 22 and the hub has anchoring members 231, 232 at its periphery that faces into the slit. Here these anchoring regions are shown in optional forms of a key-way 231 and a planar face 232. Key-way 231 is in the form of an axially extending slot that extends in a rear direction from the key-way's forward opening 2312. The key-way's slot is adapted to ensure correct orientation with other parts that can be fitted therein in the axial direction. The anchoring regions are also seen including a planar face 2311 formed at a radial outer side of the slit 22 opposite to key-way 231 in order to interact with such other parts that may be fitted into the key-way to ensure their correct orientation. The anchoring regions may also include an outer planar face 2321 formed at a radial outer side of the slit 22 opposite planar face 232 in order to interact with other parts that may be fitted in between the planar faces 232, 2321 to ensure their correct orientation. Notably, the device's coupling region is adapted to receive parts that are urged rearward along the device's axis X in order to interact and engage with one or more of its anchoring regions.

The self-imaging device includes in addition a guide element (only tip 241 being seen) that extends from an axial rear tip where a camera is located (rear tip and camera not shown) to an axial forward tip 241 that opens out at a center of the hub. The camera is arranged to image in an axial forward direction via tip 241 and a plurality of light sources 242, such as LED's, may be located about tip 241 and arranged to provide illumination in an axial forward direction.

Attention is drawn to FIGS. 3A and 3B schematically illustrating an ancillary member 26 that can be fitted to coupling region 18 of the self-imaging device. Ancillary member 26 in this example may be suited for imaging within the nasal cavity, however similar type members may be arranged e.g. as earpods configured to be at least partially inserted into an ear of a person for imaging within the ear.

Ancillary member 26 is here seen formed about an axis Y and includes an internal passage 261 that opens out at both its axial ends. An axial rear side of ancillary member 26 may be provided with structures suitable for mating with at least some of the anchoring regions 231, 2311, 2312, 232, 2321 in the device's coupling region 18. In this example, such structure may be embodied as a key 263 and a first planar face 264 and a second planar face 2641 that are arranged to respectively mate with the anchoring regions 231, 2311, 2312, 232, 2321. The first planar face 264 is formed on a rear peripheral outer side of the ancillary member 26 that is displaced relative to key 263 by about 180 degrees about axis Y. The second planar face 2641 is located on a rear peripheral outer side of the ancillary member 26 adjacent key 263 and radially outward relative to the key. Ancillary member 26 as seen tapers in a forward direction to its axial forward end to assist its placemat within a cavity of a body.

When coupled together, the axes X, Y of the self-imaging device and the ancillary member are arranged to be generally collinearly aligned, and the self-imaging device may then be suited to illuminate and image structures within a targeted body portion through the internal passage 261 of ancillary member 26. After generally aligning the axes X, Y—ancillary member 26 may be urged rearward to enter into mating engagement with the anchoring regions 231, 2311, 2312, 232, 2321 of the self-imaging device.

Attention is drawn to FIGS. 4A and 4B schematically illustrating an embodiment of an ancillary member 28 that can be fitted to coupling region 18 of the self-imaging device. Ancillary member 28 in this example may be suited for acting as a tongue depressor element for assisting in imaging within a person's mouth. Ancillary member 28 here includes a rear extending shaft 281 that can be suited to mate with the key-way anchoring member 231 and planar face 2311 of coupling region 18 by inserting the shaft 281 with its rear end leading via opening 2312 axially into the slot of the key-way. In addition, ancillary member 28 includes a generally flat formation 282 at its forward side for engaging with the tongue of a mouth being imaged.

Attention is drawn to FIGS. 5A to 5C scenically illustrating an embodiment of an ancillary member 30, in this example generally formed as a pacifier, which can be fitted to coupling region 18 of the self-imaging device.

Ancillary member 30 is also formed about an axis Y and includes an internal passage 261 that opens out at both its axial ends. An axial rear side of ancillary member 30 may be provided with structures suitable for mating with at least some of the anchoring regions 231, 2311, 2312, 232, 2321 in the device's coupling region 18. In this example, such structure may be embodied as a key 263 and a first planar face 264 and a second planar face 2641 that are arranged to respectively mate with the anchoring regions 231, 2311, 2312, 232, 2321. The first planar face 264 is formed on a rear peripheral outer side of the ancillary member 30 that is displaced relative to key 263 by about 180 degrees about axis Y. The second planar face 2641 is located on a rear peripheral outer side of the ancillary member 30 adjacent key 263 and radially outward relative to the key.

Passage 261 of ancillary member 30 may be formed with a canal 2611 that passes through a generally deformable elongated teat portion 301 of member 30 that an infant suckles upon. Canal 2611 may be formed form a stiffer and relatively less deformable material than the surrounding teat portion 301 so that when an infant suckles upon the teat portion the canal 2611 will maintain a generally straight line of sight along axis Y so that an interior of an infant's mouth may be imaged by the self-imaging device to which ancillary member 30 is coupled. After generally aligning the axes X, Y—ancillary member 30 may be urged rearward to enter into mating engagement with the anchoring regions 231, 2311, 2312, 232, 2321 of the self-imaging device.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

Furthermore, while the present application or technology has been illustrated and described in detail in the drawings and foregoing description, such illustration and description are to be considered illustrative or exemplary and non-restrictive; the technology is thus not limited to the disclosed embodiments. Variations to the disclosed embodiments can be understood and effected by those skilled in the art and practicing the claimed technology, from a study of the drawings, the technology, and the appended claims.

In the claims, the word "comprising" does not exclude other elements or steps, and the indefinite article "a" or "an"

does not exclude a plurality. A single processor or other unit may fulfill the functions of several items recited in the claims. The mere fact that certain measures are recited in mutually different dependent claims does not indicate that a combination of these measures cannot be used to advantage.

The present technology is also understood to encompass the exact terms, features, numerical values or ranges etc., if in here such terms, features, numerical values or ranges etc. are referred to in connection with terms such as "about, ca., substantially, generally, at least" etc. In other words, "about 3" shall also comprise "3" or "substantially perpendicular" shall also comprise "perpendicular". Any reference signs in the claims should not be considered as limiting the scope.

Although the present embodiments have been described to a certain degree of particularity, it should be understood that various alterations and modifications could be made without departing from the scope of the invention as hereinafter claimed.

The invention claimed is:

1. A self-imaging device for imaging a body portion and having a longitudinal axis and comprising an axially extending base, a camera located within the base and a guide element for transmitting light along a path that extends between the camera and an exposed tip of the guide element that opens out to an exterior of the self-imaging device, wherein
   the base is configured to be manually held and operated by a user imaging his own body portion and the self-imaging device comprising a coupling region at an axial forward side of the base that is configured for coupling to ancillary devices,
   the exposed tip of the guide element is located in a hub portion that is comprised in the coupling region, the hub portion being surrounded by a peripheral slit,
   the coupling region comprises anchoring members at a periphery of the hub portion that face into the slit for ensuring a pre-defined orientation that an ancillary device can be coupled to the coupling region, the anchoring members at the periphery of the hub portion comprise a key-way and a planar face,
   the key-way being in form of an axially extending slot that extends in a rear direction from a forward opening of the key-way,
   the coupling region comprises further anchoring members in form of a planar face formed at a radial outer side of the slit opposite to key-way and an outer planar face formed at a radial outer side of the slit opposite the planar face on the outer periphery of the hub portion.

2. The self-imaging device of claim 1, comprising a plurality of light sources formed around the exposed tip of the guide element.

3. The self-imaging device of claim 2, wherein the exposed tip of the guide element is arranged to receive light along a straight axis that extends away from the self-imaging device and the light sources are arranged to provide illumination generally alongside this same straight axis.

4. The self-imaging device of claim 3, wherein the camera is arranged to record images or videos.

5. The self-imaging device of claim 4, wherein data recorded by the camera is arranged to be transmitted out of the self-imaging device, and wherein the self-imaging device being connected to a local computing device for transmitting the data to the local computing device.

6. The self-imaging device of claim 5 and being arranged to communicate with a remote computing device for displaying the data on the remote computing device.

7. A system for self-imaging a body portion comprising a manually held self-imaging device and an ancillary device that is attachable to the self-imaging device, the self-imaging device having a longitudinal axis and comprising an axially extending base, a camera located within the base and a guide element for transmitting light along a path extending between the camera and an exposed tip of the guide element that opens out of the self-imaging device at an axial forward side of the device, wherein the ancillary device is arranged to attach to the self-imaging device at said axial forward side while substantially not obstructing incoming light arriving towards the self-imaging device from being transmitted via the guide element towards the camera,
   the self-imaging device comprising a coupling region at the axial forward side of base for coupling to the ancillary device,
   the exposed tip of the guide element is located in a hub portion that is comprised in the coupling region, the gub portion being surrounded by a peripheral slit,
   the coupling region comprises anchoring membrs at a periphery of the hub portion that face into the slit for ensuring a pre-defined orientation that the ancillary device can be coupled to the coupling region, the anchoring members at the periphery of the hub portion comprise a key-way and a planar face,
   the key-way being in form of an axially extending slot that extends in a rear direction from a forward opening of the key-way,
   the coupling region comprises further anchoring members in form of a planar face formed at a radial outer side of the slit opporite to key-way and an outer planar face formed at a radial outer side of the slit opposite the planar face on the outer periphery of the hub portion,
   said further anchoring members also being configured for ensuring a pre-defined orientation that the ancillary device can be coupled to the coupling region.

8. The system of claims 7, comprising a plurality of light sources formed around the exposed tip of the guide element.

9. The system of claim 8, wherein the exposed tip of the guide element is arranged to receive light along a straight axis that extends away from the self-imaging device and the light sources are arranged to provide illumination generally alongside this same straight axis.

10. The system of claim 9, wherein the camera is arranged to record images or videos.

11. The system of claim 7, wherein data recorded by the camera is arranged to be transmitted out of the system.

12. The system of claim 11, wherein the self-imaging device is connected; to a local computing device for transmitting the data to the local computing device.

13. The system of claim 11 and being in communication with a remote computing device for displaying the data on the remote computing device.

14. The system of claim 7, wherein the ancillary device comprises a through going internal passage and the incoming light arriving towards the self-imaging device passes through the passage.

15. The system of claim 14, wherein the ancillary device being configured for imaging within any one of: a nasal cavity, an ear, and/or a mouth.

16. The system of claim 7, wherein the ancillary device is attachable to the self-imaging device via only some of the anchoring members.

* * * * *